US00PP10984P

United States Patent [19]

Chamberlin, Sr.

[11] Patent Number: Plant 10,984

[45] Date of Patent: Jun. 29, 1999

[54] PLUM TREE NAMED '315-80-67'

[75] Inventor: Thomas O. Chamberlin, Sr., Visalia, Calif.

[73] Assignee: Agri Sun Nursery, L.L.C., Selma, Calif.

[21] Appl. No.: 09/022,637

[22] Filed: Feb. 12, 1998

[51] Int. Cl.[6] ..... A01H 5/00

[52] U.S. Cl. ..... Plt./184

[58] Field of Search ..... Plt./184

[56] References Cited

U.S. PATENT DOCUMENTS

P.P. 6,380 11/1988 Bubani ..... Plt./184

P.P. 10,385 5/1998 Zaiger etal. ..... Plt./184

*Primary Examiner*—Howard J. Locker

*Assistant Examiner*—Wendy Anne Baker

*Attorney, Agent, or Firm*—Burns, Doane, Swecker & Mathis, L.L.P.

[57] ABSTRACT

A new and distinct cultivar of plum tree (i.e., *Prunus domestica*) is provided that forms in abundance attractive dark red mature fruit that is more long than round. The fruit flesh possesses a crisp firmness and is of a nicely contrasting light yellow coloration. The fruit base well resists cracking at the suture line and the fruit commonly is readly for harvest at approximately August $10^{th}$ to $20^{th}$ at Fresno, Calif. The new cultivar is not self-fruiting and requires another plum tree for fertilization. The fruit crop formed on the new cultivar possesses mild to sweet taste, handles well, keeps well, and ships well.

1 Drawing Sheet

SUMMARY OF THE INVENTION

The present invention is directed to a new and distinct plum (i.e., *Prunus domestica*) cultivar that originated as a chance seedling on nursery property located at Del Rey, Calif. The plum seed used in the planting was of unknown parentage and was obtained from open-pollinated plum trees growing in the same general area. Further information concerning the origin of the seed is not avaiable. It was the goal of the originator to grow out such seeds in the search of an attractive new plum cultivar that is well suited for commercial plum production under California growing conditions.

The seed that resulted in the formation of the new cultivar was collected during the late summer of 1979 and was planted in the nursery during the early spring of 1980. The first fruit was observed during late summer of 1983 and its attractive and distinctive nature was duly noted. Had my efforts including the growing and study of the resulting seedlings not led to the discovery and preservation of the new cultivar of the present invention, it would have been lost to mankind.

It was found that the new plum cultivar of the present invention exhibits the following combination of characteristics:

(a) is not self-fruiting and requires another plum tree for fertilization, (b) produces in abundance a fruit crop that commonly is ready for harvest during mid-August at the Fresno, Calif. area, and (c) forms dark red mature fruit that is more long than round having a light yellow firm flesh which ships and stores well.

The new cultivar of the present invention is particularly well suited for producing a quality plum crop that matures during mid-August at the indicated growing area. For instance, when grown at the Fresno, Calif., growing area, harvest dates commonly range from August $10^{th}$ to August $20^{th}$. The fruit has an attractive dark red appearance and the crisp flesh is a nicely contrasting light yellow coloration. The fruit diameter commonly is approximately 2 5/16 to 2 7/16 inches. The fruit shape is not full-round, and is more long than round (as illustrated). The fruit flavor is a pleasing mild to sweet and is fully developed at harvest time. The new cultivar has never been observed to be self-fruiting, but nevertheless has been found to bear a heavy crop when planted with other plum trees. Cracks have not been observed on the fruit base at the suture line. Also, no sunburn of the fruit flesh has been observed. The fruit has been kept in cold storage for as many as 30 days and has retained its desired firmness. Also, the fruit has been stored on the shelf for nearly two weeks in the absence of cold storage while retaining its desirable characteristics.

Asexual reproduction by budding at Selma, Calif. has demonstrated that the characteristics of the new cultivar are firmly fixed and are reliably transferred from one generation to another. Budwood was first collected from the seedling of the new cultivar during the winters of 1986 and 1987. Seedlings were budded in the early spring in 1989. The fruit formed on the budded trees was observed to be the same as that formed on the parent tree of the new cultivar. Subsequent asexual propagation has confirmed the results that initially were obtained.

The new cultivar of the present invention has been named '315-80-67', and is being marketed under the Red Sun trademark.

BRIEF DESCRIPTION OF THE PHOTOGRAPH

The accompanying photograph shows specimens of the foliage and fruit of the new cultivar at maturity as depicted in color as nearly true as its is possible to make the same in a color illustration of this character. The plant was grown at Selma, Calif. The mature dark red fruit with light yellow flesh is shown. The slightly more long than round fruit configuration is apparent.

DETAILED DESCRIPTION

The following is a detailed description of the new cultivar obtained from first generation budded trees of the new '315-80-67' cultivar growing on property of Agri Sun Nursery L.L.C. at Selma, Calif. Color designations are with reference to the Color Name Chart of the Inter-Society Color Council, National Bureau of Standards.

Botanical classification: *Prunus domestica*, cv. '315-80-67'.

Tree:

*Size.*—Typical for plum trees depending on the nature of shaping and pruning.

*Productivity.*—Very good, not self-fruiting and sets a heavy crop when grown with other plum trees.

*Trunk.*—Diameter: typical for plum trees. Surface characteristics: medium rough with long vertical slits, commonly with approximately 10 to 12 lenticels per square inch having a diameter of approximately 1/8 inch and a coloration of 74 s.y.b. Bark: dark yellow brown (78 d.y.b.).

Branches:

*Size.*—Typical for plum trees and depending on the nature of shaping and pruning.

*Color.*—Dark yellow brown (78 d.y.b.).

*Lenticels.*—Commonly measure approximately 1/8 inch, commonly are present at a frequency of approximately 10 to 12 per square inch, and commonly are 74 s.y.b. in coloration.

Leaves:

*Size.*—Commonly approximately 2 3/4 to 3 1/4 inches in length and approximately 1 to 1 1/4 inch in width.

*Configuration.*—Lanceolate.

*Color.*—Dark green (125 m.dk.g.) on the upper surface and light green (136 m.y.g.) on the under surface.

*Margins.*—Serrate.

*Leaf base.*—Crenate.

*Stem glands.*—None observed to date.

*Petioles.*—Size: approximately 1/2 inch in length and approximately 1/16 inch in width.

Flower buds (observed as white starts to show at the apex):

*Size.*—Commonly approximately 3/16 inch in diameter and approximately 3/16 inch in length.

*Petiole length.*—Commonly approximately 1/8 inch in length.

*Configuration.*—Substantially round.

*Color.*—Primarily light green (136 m.y.g.).

*Bearing.*—Commonly with a medium flower and bud set on fruit spurs that are closely positioned on the branch.

Flowers:

*Date of bloom.*—Commonly approximately February 25$^{th}$ to 28$^{th}$ at Selma, Calif.

*Petal size.*—Approximately 5/16 inch in length and 1/4 inch in width, and appear to be substantially round.

*Color.*—White (263 white).

*Stem length.*—Commonly approximately 5/16 inch.

Fruit:

*Date of maturity.*—Commonly approximately August 10$^{th}$ to 20$^{th}$ at Selma, Calif.

*Uniformity.*—Good.

*Size.*—Commonly approximately 2 5/16 to 2 7/16 inches in diameter, approximately 2 7/16 inches transverse to the suture plane, and approximately 2 5/16 to 2 7/16 inches transverse at a right angle to the suture plane.

*Configuration.*—Almost round but slightly more long than round.

*Suture.*—Smooth and slightly recessed, and the length from the stem cavity to the pistil point commonly is approximately 3 3/4 inches.

*Ventral surface.*—Rounded.

*Stem cavity.*—Slightly elongated, approximately 3/8 in width and approximately 1/4 inch in depth.

*Base.*—Commonly wide and round.

*Apex.*—Rounded.

*Pistil point.*—Smooth.

*Stem.*—Commonly approximately 7/16 inch in length and approximately 1/16 inch in width.

Fruit skin:

*Thickness.*—Typical for a plum.

*Texture.*—Smooth.

*Tendency to crack.*—None.

*Color.*—Dark red (17 v.d.r.).

Fruit flesh:

*Color.*—Light yellow to off-white (89 p.y.).

*Surface of pit well.*—Nearly smooth.

*Color of pit well.*—Orange-yellow (72 d.oy.).

*Juice production.*—Very juicy.

*Flavor.*—Mild to sweet.

*Aroma.*—Slight.

*Texture.*—Crisp and smooth.

*Fibers.*—None.

*Ripening.*—Substantially even throughout.

*Eating quality.*—Good.

Stone:

*Freeness.*—Free.

*Fibers.*—None.

*Color.*—Yellow (72 d.oy.).

*Size.*—Commonly approximately 5/16 inch in length, 5/8 inch in width, and approximately 3/8 inch in thickness.

*Configuration.*—Elongated and somewhat flattened in appearance.

*Base.*—Elongated and commonly approximately 1/4 inch in length, and approximately 1/16 inch in width with almost smooth sides and the absence of ridges.

Use: Fresh market.

Keeping quality: Very good, has kept well in cold storage for 30 days.

Shipping quality: Very good in view of inherently crisp firm nature.

Disease resistance: No disease susceptibility has been noted to date.

Although the new '315-80-67' cultivar of plum tree possesses the above-described characteristics as a result of the growing conditions at Selma, Calif., it is to be expected that variations of the usual type and magnitude may appear that are caused by differences in growing conditions, fertilization, pruning, pest control and other horticultural practices when the new cultivar is grown in different environments.

I claim:

1. A new and distinct plum cultivar having the following combination of characteristics:

(a) is not self-fruiting and requires another plum tree for fertilization, (b) produces in abundance a fruit crop that commonly is ready for harvest during mid-August at the Fresno, Calif. area, and (c) forms dark red mature fruit that is more long than round having light yellow firm flesh which ships and stores well;

substantially as herein shown and described.

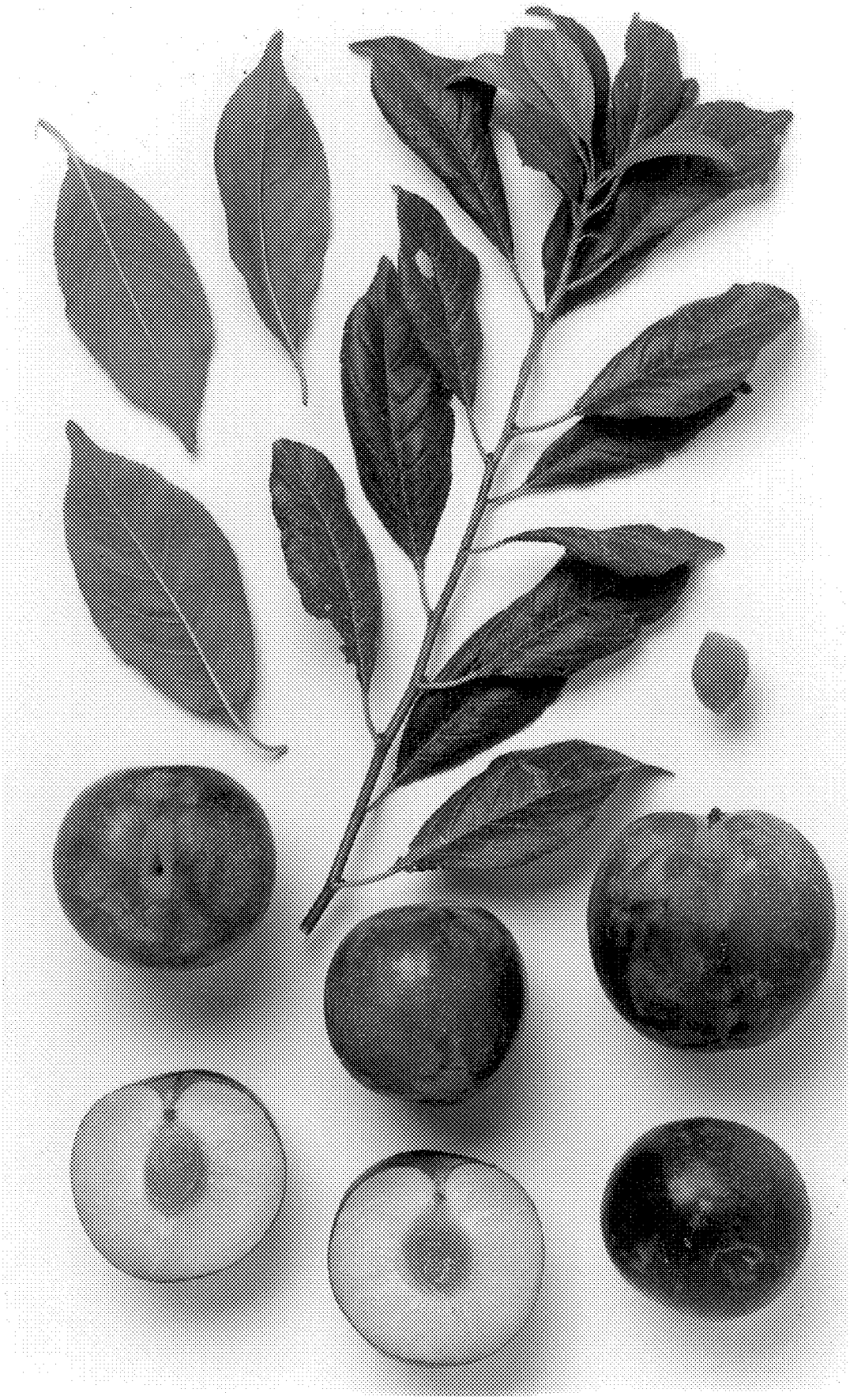

* * * * *